US005245064A

United States Patent [19]

Gassman et al.

[11] Patent Number: 5,245,064

[45] Date of Patent: Sep. 14, 1993

[54] 1,2,3,4-TETRAALKYL-5-PERFLUOROAL-KYL-CYCLOPENTADIENE, DI-(PERFLUOROALKYL)-TRIALKYLCY-CLOPENTADIENE AND TRANSITION METAL COMPLEXES THEREOF

[76] Inventors: Paul G. Gassman; John R. Sowa, both of St. Paul; John W. Mickelson, Kalamazoo, all of Minn.

[21] Appl. No.: 929,959

[22] Filed: Aug. 14, 1992

[51] Int. Cl.$^5$ .................... C07F 17/02; C07F 11/00; C07F 13/00; C07C 1/207
[52] U.S. Cl. ......................................... 556/60; 556/1; 556/43; 556/47; 556/53; 556/136; 556/112; 556/142; 556/143; 585/359; 534/15
[58] Field of Search ............... 556/1, 43, 53, 47, 60, 556/136, 142, 143, 112; 585/359; 534/15

[56] References Cited

U.S. PATENT DOCUMENTS 4,699,987 10/1987 Gassman et al. ................. 556/1

OTHER PUBLICATIONS

F. G. Bordwell et al., *J. Amer. Chem. Soc.*, 79, 1593 (1957).
N. C. Deno, *J. Am. Chem. Soc.*, 86, 1871 (1964).
T. S. Sorensen, *Can J. Chem.*, 43, 2744 (1965).
R. B. Woodward et al., *J. Am. Chem. Soc.*, 87, 395 (1965).
T. S. Sorensen, *Can J. Chem.*, 43, 2744 (1965).
N. C. Deno et al., *J. Am. Chem. Soc.*, 87 2153 (1965).
R. B. King et al., *J. Organomet. Chem.*, 8, 287 (1967).
T. S. Sorensen, *J. Am. Chem. Soc.*, 89, 3782 (1967).
T. S. Sorensen, *J. Am. Chem. Soc.*, 89, 3794 (1967).
P. H. Campbell et al., *J. Amer. Chem. Soc.*, 91, 6404 (1969).
J. W. Kang et al., *J. Am. Chem. Soc.*, 91, 5970 (1969).
R. B. King et al., *J. Organometallic Chem.*, 69, 131 (1974).
R. B. King, *Coord. Chem. Rev.*, 20, 155 (1976).
A. Bond et al., *J. Chem. Soc., Dalton Trans.*, 2372 (1977).
R. S. Threlkel et al., *J. Organometallic Chem.*, 136, 1 (1977).
P. M. Maitlis et al., *Acc. Chem. Res.*, 11, 301 (1978).

D. P. Freyberg et al., *J. Am. Chem. Soc.*, 101, 892 (1979).
G. Bott et al., *J. Am. Chem. Soc.*, 102, 5618 (1980).
D. J. Sikora et al., *J. Am. Chem. Soc.*, 103, 1265 (1981).
D. C. Calabro et al., *J. Am. Chem. Soc.*, 103, 6839 (1981).
D. W. Macomber et al., *Advances in Organometallic Chemistry*, 21 (1982) at pp. 4-28.
P. G. Gassman et al., *Organometallics*, 2, 1470 (1983).
M. E. Rerek et al., *J. Am. Chem. Soc.*, 106, 5908 (1984).
G. Jeske et al., *J. Am. Chem. Soc.*, 107, 8091 (1985).
H. Bonnemann, *Angew. Chem. Int. Ed. Engl.*, 24, 248 (1985).
M. O. Albers et al., *Organometallics*, 5, 2321 (1986).
P. G. Gassman et al., *J. Am. Chem. Soc.*, 108, 4228 (1986).
P. G. Gassman et al., *J. Am. Chem. Soc.*, 110, 6130 (1988).
M. J. Burk et al., *J. Amer. Chem. Soc.*, 113, 2537 (1990).
J. R. Sowa et al., *J. Am. Chem. Soc.*, 113, 2537 (1990).
P. G. Gassman et al., *Organometallics*, 10, 1592 (1991).
P. G. Gassman et al., *J. Org. Chem.*, 56, 5143 (1991).

*Primary Examiner*—José G. Dees
*Assistant Examiner*—Perfirio Nazario-Gonzalez
*Attorney, Agent, or Firm*—Merchant, Gould, Smith, Edell, Welter & Schmidt

[57] ABSTRACT

The present invention provides a compound of the formula:

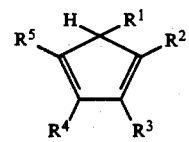

wherein $R^1$ is $(C_1-C_5)$perfluoroalkyl, $R^2$ is $(C_1-C_5)$perfluoroalkyl or $(C_1-C_5)$alkyl, $R^3$ is $(C_1-C_5)$perfluoroalkyl or $(C_1-C_5)$alkyl, $R^4$ is $(C_1-C_5)$alkyl and $R^5$ is $(C_1-C_5)$alkyl, with the proviso that no more than two of $R^1$, $R^2$ and $R^3$ can be $(C_1-C_5)$perfluoroalkyl; and transition metal complexes thereof.

29 Claims, 1 Drawing Sheet

FIG. 1

1,2,3,4-TETRAALKYL-5-PERFLUOROALKYL-CYCLOPENTADIENE, DI-(PERFLUOROALKYL)-TRIALKYLCYCLOPENTADIENE AND TRANSITION METAL COMPLEXES THEREOF

This invention was made with the support of National Science Foundation Grant No. CHE-8921744. The U.S. Government has certain rights in the invention.

BACKGROUND OF THE INVENTION

Since the discovery of the first cyclopentadienyl transition metal compound, ferrocene, considerable effort has been expended to evaluate the effects of substituents located on the cyclopentadienyl moiety (Cp) on the electronic character of the transition metals complexed thereto. In terms of substituents, most attention has been devoted to the pentamethylcyclopentadienyl moiety (Cp*).

Pentamethylcyclopentadiene was first synthesized in 1967 by R. B. King et al., *J. Organomet. Chem.*, 8, 287 (1967). Since, it has been widely used as a ligand for a broad range of transition metals. See, for example, P. M. Maitlis et al., *Acc. Chem. Res.*, 11, 301 (1978). The presence of the methyl groups serves two purposes. First, the methyl groups sterically encumber and hinder the complexed transition metal, thus protecting it from attack by bulky reagents. Second, the five methyl groups significantly alter the electronic character of the complexed transition metal through electron donation by the methyl groups which is enhanced relative to that provided by hydrogen as a substituent on cyclopentadiene complexes. See P. G. Gassman et al., *Organometallics*, 2, 1470 (1983).

By comparison, relatively little is known about the properties of transition metal complexes incorporating cyclopentadienyl ligands bearing electron-withdrawing substituents. See D. W. Macomber et al., *Advances in Organometallic Chemistry*, 21 (1982) at pages 4-28.

The preparation of a few transition metal complexes comprising trifluoromethylcyclopentadienyl ligands has been reported. For example, the synthesis of trifluoromethylcyclopentadienyl(cyclooctadienyl) cobalt from a halotris(triorganophosphine)cobalt(I) complex has been reported, and trifluoromethylcyclopentadienyl thallium has been patented (U.S. Pat. No. 4,699,987). In 1977, A. Bond et al., cited below, reported the preparation of the dimer of 1-perfluoroalkyl-2,3,4,5-tetramethylcyclopentadienyl-iron tricarbonyl via the irradiation of a solution of tetramethylcyclobutadientyliron tricarbonyl and trifluoromethylacetylene, followed by thermolysis of the reaction product. Tetrakis(trifluoromethyl)cyclopentadienide complexes of ruthenium have also been prepared by M. J. Burk et al., *J. Amer. Chem. Soc.*, 111, 8939 (1989). However, cyclopentadienyl ligands bearing trifluoromethyl groups have not been widely developed as transition metal ligands. This is surprising, in view of the desirability of the use of cyclopentadienyl complexes which include electron-withdrawing substituents in certain catalytic processes. For example, the ability of a series of (cyclopentadienyl)(cyclooctadienyl)cobalt complexes to catalyze pyridine and/or xylene ring formation from a mixture of ethyl cyanide and propyne was found to increase as the electron-withdrawing strength of the substituent on the cyclopentadienyl ring increased. Increased electron density at the cobalt atom resulted in a reduction of the catalyst activity of the cobalt complex. In contrast, electron-withdrawing substituents lowered the electron density at the cobalt atom, and the deshielded cobalt "core" exhibited higher catalytic activity. Thus, in this series, the pentamethylcyclopentadienyl system exhibited the lowest catalytic activity in the test reaction, whereas the highest activity at 65% propyne conversion was found for the benzoylcyclopentadienyl system, which was 1,000 times more reactive. See H. Bonnemann, *Angew. Chem. Int. Ed. Engl.*, 24, 248 (1985).

Because electronic effects can dramatically influence chemical behavior, a need exists for cyclopentadienide ligands with the steric bulk provided by pentaalkyl (for instance, pentamethyl or pentaethyl), in combination with the relative electronic character of unsubstituted cyclopentadienide or the electron deficiencies provided by mono- or di-trifluoroalkyl substituents. Transition metal complexes wherein the transition metal is complexed to such sterically encumbered but electronically neutral (or electron deficient) ligands may be useful in a wide variety of catalytic processes, such as the Ziegler-Natta polymerization of ethylene and propylene, acetylene trimerization, carbon-hydrogen activation, hydrogenation and the like.

SUMMARY OF THE INVENTION

The present invention provides three novel substituted cyclopentadienes which are useful to form a wide variety of monomeric and dimeric transition metal complexes, wherein the transition metal or metals are optionally complexed to additional ligands, such as phosphines, halo, carbonyl and the like. Thus, the present invention is directed to compounds of the general formula (I):

and the two endocyclic double bond isomers thereof, wherein $R^1$ is $(C_1-C_5)$perfluoroalkyl, $R^2$ is $(C_1-C_5)$perfluoroalkyl or $(C_1-C_5)$alkyl, $R^3$ is $(C_1-C_5)$perfluoroalkyl or $(C_1-C_5)$alkyl, $R^4$ is $(C_1-C_5)$alkyl and $R^5$ is $(C_1-C_5)$alkyl, with the proviso that no more than two of $R^1$, $R^2$ and $R^3$ can be $(C_1-C_5)$perfluoroalkyl. Preferably, $(C_1-C_5)$perfluoroethyl$(C_2F_5)$, and $(C_1-C_5)$alkyl is methyl or ethyl. For example, a preferred compound of the present invention is 1,2,3,4-tetramethyl-5-trifluoromethylcyclopentadiene of formula (1):

Another preferred compound is 1,2,4-trimethyl-3,5-bis(trifluoromethyl)cyclopentadiene (1A):

1A

Another preferred compound of the invention is 1,2-bis(trifluoromethyl)-3,4,5-trimethylcyclopentadiene (1B).

Although depicted as a single derivative of cyclopentadiene for convenience, it is to be understood that these compounds includes mixtures of the 3 possible olefinic isomers in each case. The present invention also provides transition metal complexes of the formula (II):

II wherein M is a metal selected from Group IIIB, IVB, VB, VIB, VIIB, VIII, or IB, preferably from Group VIB, VIIB or VIII, $n=1-5$, preferably 1-3, and each L is a ligand selected so that all L donate a total number of electrons to the metal, to provide the metal with a total of 16-18 electrons in the valence shell of the metal; and the salts thereof.

Thus, when $n=3$, each L is a two-electron donor ligand, such as CN, CO, or a substituted phosphine; when $n=2$, one ligand is a bidentate four-electron donor, such as a bis(phosphine), and the other ligand is a two-electron donor, and when $n=1$, L is a tridentate six-electron donor, such as a tris(phosphine), cyclopentadienyl, or substituted cyclopentadienyl.

Thus, the present invention also provides monomeric and dimeric transition metal complexes of the formulas B and C, below:

(B)

(C)

and the acid addition salts thereof, wherein $R^1$, $R^2$, $R^3$, $R^4$ and $R^5$ are as described above, M is a transition metal, i.e., a Group IIIB, IVB, VB, VIB, VIIB, VIII or IB metal, preferably a group VIB, VIIB or VIII metal and $L^1$, $L^2$, $L^3$, $L^4$, and $L^5$ are electron donor ligands selected so that M has a 16, 17 or 18 electron outer shell configuration. Preferably, complexes II, B and C are neutral in charge.

L ($L^1$-$L^5$) may each be discrete two-electron donor ligands selected from the group consisting of a trivalent amine, phosphine, arsine, and a stibene of the general formulae $(R)_3N$, $(R)_3P$, $(R)_3As$ or $(R)_3Sb$, respectively, wherein each R is H, halo, alkyl, perfluoroalkyl, alkoxy, aryloxy, acyl, or aryl, and is selected so that the amine, phosphine, arsine or stibene contains a total of about 0 to 30 carbon atoms; phosphites $((RO)_3P$, wherein each R is alkyl, perfluoroalkyl or aryl and is selected so that the phosphite contains 3 to 30 carbon atoms; a divalent ether (ROR), a thiol (RS), an alkoxy (RO-), a sulfide (RSR), a nitrile (RCN), or an isonitrile (RNC), wherein each R is alkyl, perfluoroalkyl, or aryl and is selected so that the ether, thiol, alkoxy, sulfide, nitrile, or isonitrile contains 2-30 carbon atoms; an olefin $((R)_2C=C(R)_2)$, or an acetylene (RCCR), wherein each R is H, halo, alkyl, perfluoroalkyl, —CHO, —Cn, (tri($C_1$-$C_4$)alkyl)-silyl or aryl, and is selected so that the olefin or acetylene has 2-30 carbon atoms; ($C_1$-$C_5$)alkyl, hydride (H), nitrosyl (NO), halo, cyano (CN), water ($H_2O$), and thiocarbonyl (CN).

In the complex of formula II, when $M=Fe$, $n=3$ and two L are carbonyl, the remaining L cannot be H. In the complex of formula II, when $M=Fe$ and one L is $\{\eta^5\text{-}(1,2,3,4\text{-tetramethyl-5-trifluoromethylcyclopentadiene})\}Fe\text{-}(CO)_2$, the remaining two L cannot be carbonyl.

In the complex of formula B, when M is Fe, and $L^1$ and $L^2$ are carbonyl, $L^3$ cannot be H. In the complex of formula C, when M is Fe, $L^1$ and $L^3$ cannot be CO.

$L^1$, $L^2$ and $L^3$ taken together can also be an aromatic ligand which is a five- or six-electron donor, such as the anion of a second molecule of I, $\eta^5$-cyclopentadienide, $\eta^5$-methylcyclopentadienide, $\eta^5$-pentamethylcyclopentadienide, $\eta^5$-trifluoromethylcyclopentadienide, or penta(trifluoromethyl)cyclopentadienide, an $\eta^5$-indenide, $\eta^5$-fluorenide or an $\eta^6$-($C_6$-$C_{12}$)arene, such as benzene, anisole, chlorobenzene, naphthalene, hexamethylbenzene, toluene, hexamethylbenzene or 1,3,5-trimethylbenzene.

$L^1$ and $L^2$ taken together can be a bidentate, four-electron donor ligand, such as acetylacetonate, 2,2'-bipyridyl, or a diene, i.e., butadiene, 2,3,-dimethylbutadiene, cyclooctadiene or norbornadiene; or a bidentate phosphine or arsine ligand of the general formula $(R)_2X(Y)X(R)_2$ perfluoroalkyl or ($C_6$-$C_{10}$)aryl and Y is ($C_1$-$C_4$) alkylene, ($C_2$-$C_4$)alkylidene or o-phenylene. Useful bidentate ligands of this type include 1,2-bis(diethylphosphine)ethane, 1,2-bis(diethylphosphine)methane, o-phenylenebisdimethylarsine, 1,2-bis(diphenylphosphino)ethane, 1,2-bis(dimethylphosphino)ethane, 1,2-bis(diphenylphosphino)methane, 1,2-bis(diphenylphosphino)propane, 1,2-bis(diphenylphosphino)butane, 1-diphenylarsine-2-diphenyl-phosphinoethandiyl, and 2,2'-bis(diphenylphosphino)-1,1'-binaphthyl.

$L^1$, $L^2$ and $L^3$ taken together can be a tridentate phosphine or arsine of general formula $(R)_2X(Y)X(R).(Y)X$-$(R)_2$ wherein each X is As or P, Y is ($C_1$-$C_3$)alkylene or o-phenylene and R is ($C_1$-$C_5$)alkyl, ($C_1$-$C_5$)perfluoroalkyl or ($C_6$-$C_{10}$)aryl. Examples of tridentate ligands include tris(2-diphenylphosphinoethyl)phosphine and 1,1,1-tris(diphenylphosphinomethyl)ethane.

As used herein, with respect to the compounds of formulas B or C, the term "alkyl" includes branched or straight-chain alkyl, including ($C_1$-$C_{10}$)alkyl, or ($C_3$-$C_{10}$)cycloalkyl wherein, optionally, the carbon chain is interrupted by 1-5, preferably by about 1-2N, non-peroxide O, S, Si or mixtures thereof, e.g., by NR or SiR$_2$, wherein R is as defined for NR$_2$, above. As used herein with respect to the compounds of formulas A or B, the term "aryl" includes (C$_7$-C$_{10}$)aralkyl, or (C$_7$-C$_{10}$)alkaryl, preferably phen(C$_1$-C$_4$)alkyl or (C$_1$-C$_4$)alkyl-phenyl. The term "aryl" also includes (C$_5$-C$_6$)-membered "heteroaryl" wherein 1-3 of the ring carbon atoms have been replaced by N, O, S, Si, P or mixtures thereof. The aryl groups may also be substituted by 1-5 moieties such as halogen, preferably by F or Cl; (C$_1$-C$_4$)alkoxy, phenoxy or dioxymethylene, or by mixtures thereof.

Since, as discussed hereinabove, cyclopentadienide transition metal complexes can become more reactive with respect to the catalysis of certain reactions as the electron density of the metal is reduced, it is expected that cyclopentadienide transition metal complexes of formulas B and C will possess enhanced abilities to catalyze a variety of useful reactions, particularly Ziegler-Natta type olefin polymerizations and acetylene condensations. For example, see P. L. Pauson, *Organometallic Chemistry*, St. Martin's Press, N.Y. (1967) at Chapter 6.

The present invention also provides novel processes to prepare the compounds of formula I, as set forth below.

DETAILED DESCRIPTION OF THE INVENTION 1,2,3,4-Tetramethyl-5-(trifluoromethyl)cyclopentadiene (1) was prepared in a three-step process from trans-2-butene (2), as shown in Scheme I, below.

Scheme I

Commercially available trans-2-butene (2) was brominated-dehydrobrominated to give 3, following the procedures of P. H. Campbell et al., *J. Amer. Chem. Soc.*, 91, 6404 (1969) and F. G. Bordwell et al., *J. Amer. Chem. Soc.*, 79, 1593 (1957).

Treatment of a solution of 3 in diethyl ether at 0° C. with lithium metal resulted in metalation of 3. Addition of ethyl trifluoroacetate to this lithio derivative at −40° C. followed by quenching with dilute aqueous acid, gave an 82% yield of 4. Dehydration of 4 with methanesulfonic acid in methylene chloride at 25° C. resulted in a symmetry-allowed cyclization of the resultant carbocation to produce 1 in 82% yield as a mixture of double-bond isomers.

Figure 1:
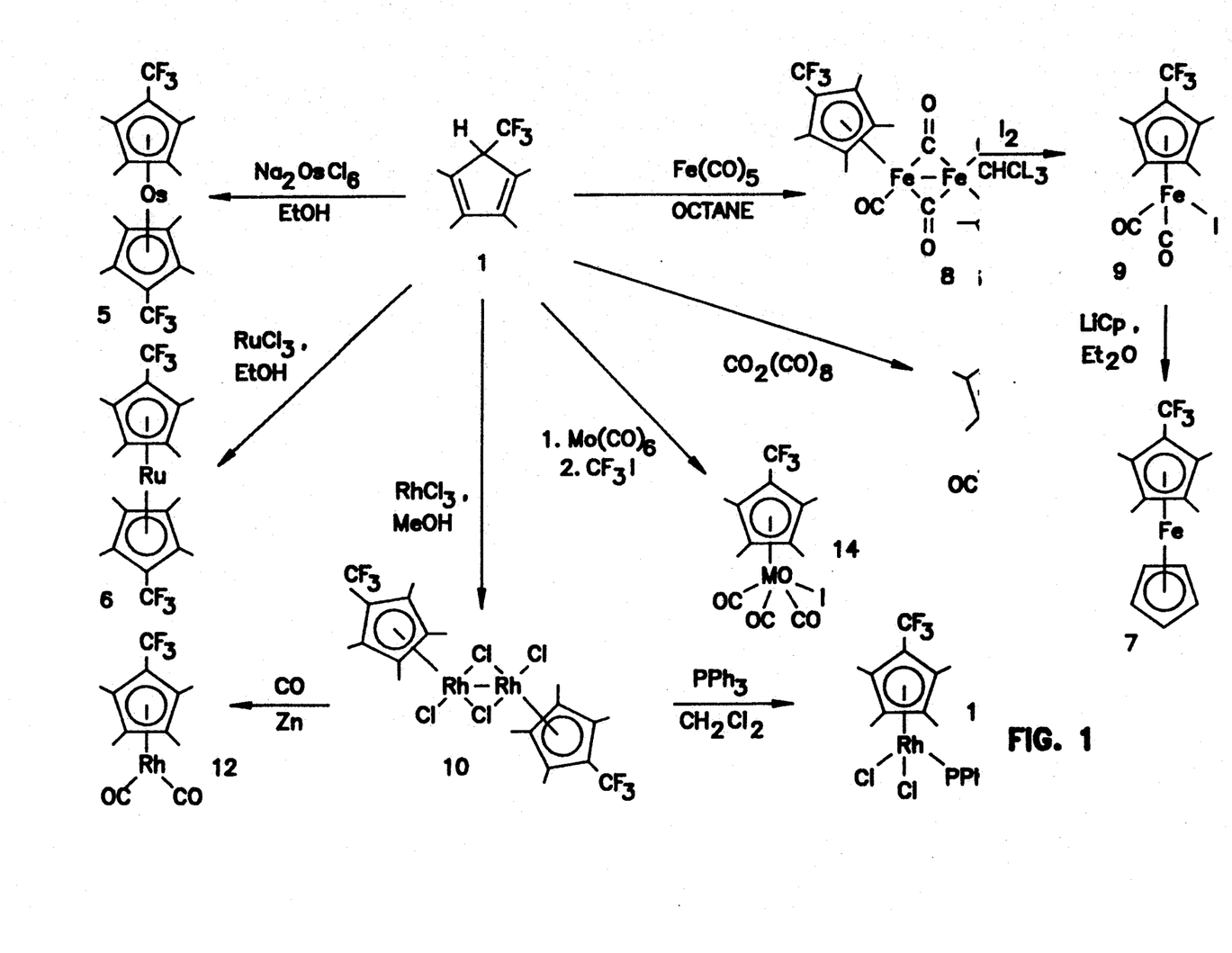
FIG. 1 is a schematic depiction of the synthesis of some of the preferred transition metal complexes of the invention from compound (1).

Neither the lithium nor thallium salts of the anion of 1 were sufficiently stable for their use as intermediates in the preparation of transition metal complexes of 1. Thus, as shown in FIG. 1, various synthetic approaches were used to prepare a series of complexes of 1 with iron, ruthenium, osmium, rhodium, cobalt and molybdenum.

The osmocene 5 and ruthenocene 6 were prepared in a straightforward manner. Treatment of excess 1 with sodium hexachloroosmate hexahydrate in refluxing ethanol for 24 hr under argon gave a 26% yield of 5. In a similar manner, ruthenium trichloride hydrate reacted with an excess of 1 in refluxing ethanol to give a 65% yield of 6. The synthesis of the unsymmetrical ferrocene 7 was less direct. Treatment of excess iron pentacarbonyl with 1 in refluxing octane gave a 34% yield of the trans dimer 8, previously reported by A. Bond et al., *J. Chem. Soc., Dalton Trans.*, 2372 (1977). On reaction with 1.1 equiv of iodine in chloroform, 8 was converted into 9 in 60% yield. Exposure of 9 to a large excess of lithium cyclopentadienide gave 7 in 18% yield.

The dimeric rhodium complex 10 was obtained in 65% yield when rhodium trichloride hydrate was treated with excess 1 in refluxing methanol. The conversion of 10 into 11 was achieved in 92% yield through treatment of 10 with a slight excess of triphenylphosphine in methylene chloride at ambient temperature.

Table I lists the inner shell electron binding energies of compounds 5-9 and 11.

TABLE I

X-ray Photoelectron Binding Energies of Pentamethylcyclopentadienide, 1,2,3,4-Tetramethyl-5-(trifluoromethyl)cyclopentadienide,[a] and Cyclopentadienide Complexes of Iron, Ruthenium, Osmium, and Rhodium

| compound | binding energy (±0.1 eV) | assignment |
|---|---|---|
| trans-[Cp*Fe(CO)$_2$]$_2$ | 707.7 | Fe(2p$_{3/2}$) |
| trans-[Cp‡ Fe(CO)$_2$]$_2$ (8)[a] | 708.1 | Fe(2p$_{3/2}$) |
| cis,trans-[CpFpe(CO)$_2$]$_2$ | 708.1 | Fe(2p$_{3/2}$) |
| Cp Fe(CO)$_2$I | 708.5 | Fe(2p$_{3/2}$) |
| Cp‡ Fe(CO)$_2$I (9) | 709.0 | Fe(2p$_{3/2}$) |
| CpFe(CO)$_2$I | 709.0 | Fe(2p$_{3/2}$) |
| Cp*$_2$Fe | 707.0 | Fe(2p$_{3/2}$) |
| Cp‡ CpFe (7) | 707.8 | Fe(2p$_{3/2}$) |
| Cp$_2$Fe | 707.8 | Fe(2p$_{3/2}$) |
| Cp*$_2$Ru | 279.7 | Ru(3d$_{5/2}$) |
| Cp‡ $_2$Ru (6) | 280.3 | Ru(3d$_{5/2}$) |
| Cp$_2$Ru | 280.3 | Ru(3d$_{5/2}$) |
| Cp*$_2$Os | 49.9 | Os(4f$_{7/2}$) |
| Cp‡ $_2$Os (5) | 50.7 | Os(4f$_{7/2}$) |
| Cp$_2$Os | 50.6 | Os(4f$_{7/2}$) |
| Cp*RhCl$_2$PPh$_3$ | 308.2 | Rh(3d$_{5/2}$) |
| Cp‡ RhCl$_2$PPh$_3$ (11) | 308.6 | Rh(3d$_{5/2}$) |
| CpRhCl$_2$PPh$_3$ | 308.6 | Rh(3d$_{5/2}$) |

[a]For the purpose of formula representation in this table, 1,2,3,4-tetramethyl-5-(trifluoromethyl)cyclopentadiene is represented as Cp‡.

For comparison purposes, the corresponding cyclopentadienyl (Cp) and pentamethylcyclopentadienyl (Cp*) complexes were purchased or prepared by literature methods, and their binding energies were measured and included in Table I. The binding energy data firmly established that 1,2,3,4-tetramethyl-5-(trifluoromethyl)-cyclopentadienide (Cp‡) is electronically equivalent to Cp. For the six series studied, the difference between Cp‡ or Cp and Cp* in electron donation to complexed transition metals ranges from 0.3 eV/Cp‡ for 6 to 0.5 eV/Cp‡ for 9. For the six series studied, the difference between Cp‡ or Cp and Cp* averaged 0.4 eV. Thus, it is obvious that the Cp‡ and Cp ligands are electronically similar, and that they are both electronically very different from Cp* when used as ligands for transition metals.

While the electronic equivalence of Cp‡ and Cp has been established, the question of steric equivalence of Cp‡ and Cp* requires examination. The literature permits the generalization that the trifluoromethyl group is larger than methyl and smaller than tert-butyl. Rotational studies suggest that trifluoromethyl is comparable in size to isopropyl or smaller than isopropyl. However, comparison of bis(trifluoromethyl)methyl with isopropyl suggests that they are very similar in size, which would imply that trifluoromethyl and methyl are close in steric effects. Clearly, Cp‡ is not a perfect steric substitute for Cp*. It is probably slightly larger. It seem likely that this difference will be sufficiently small that, for all practical purposes, Cp‡ can be viewed as sterically equivalent to Cp*.

Thus, various transition metal complexes of 1,2,-3,4-tetramethyl-5-(trifluoromethyl)cyclopentadienide have been prepared and demonstrated to be electronically equivalent to the corresponding complexes of cyclopentadienide and approximately sterically equivalent to the analogous complexes of pentamethylcyclopentadienide.

The bis(trifluoromethyl)cyclopentadiene compound (1A) was prepared as outlined in Scheme II below.

Compound 1A can be substituted for compound 1 and employed to prepare a wide variety of transition metal complexes, employing reactions such as those outlined in FIG. 1.

Compound 1B, 1,2-bis(trifluoromethyl)-3,4,5-trimethylcyclopentadiene is prepared as outlined in Scheme III, below.

The compounds of formula I can be employed to prepare a wide variety of other compounds of formula II by employing synthetic routes which have been used to prepare cyclopentadienyl metal complexes. For example, see P. L. Pauson, *Organometallic Chemistry*, St. Martin's Press, N.Y. (1967) at pages 127-155; D. W. Macomber et al., *Advances in Organometallic Chemistry*, 21, 4-28 (1982), and J. P. Collman et al., *Principles and Applications of Organotransition Metal Chemistry*, University Science Books, Mill Valley, Calif. (1987) at pages 164-175.

The invention will be further described by reference to the following detailed examples, wherein all preparative reactions, chromatography, and manipulations were carried out under an atmosphere of argon or nitrogen using standard Schlenk techniques. Methylene chloride and chloroform were distilled under argon from calcium hydride. Hexanes, pentane, diethyl ether, and tetrahydrofuran (THF) were distilled from sodium benzophenone under argon. Anhydrous ethanol and methanol were obtained by distillation from magnesium under nitrogen. A Varian VXR-300 MHz instrument was used to obtain $^1$H NMR (internal reference CHCl$_3$, $\delta=7.24$ ppm), $^{13}$C NMR (internal CDCl$_3$, $\delta=77.0$ ppm), and $^{19}$F NMR (internal reference CFCl$_3\delta=0.00$ ppm) spectra. Infrared spectra were recorded on a Mattson Instruments Polaris FT-IR spectrometer.

EXAMPLE 1

Preparation of 3,5-dimethyl,4-trifluoromethyl, 4-hydroxy-2,5-heptadiene (4)

To 6.94 g (1 mol) of lithium wire and 350 mL of anhydrous diethyl ether under a dry argon atmosphere at 0° C. was added dropwise 67.5 g (0.50 mol) of 2-bromo-cis-2-butene in 50 mL of anhydrous diethyl ether, and the reaction mixture was stirred at 0° C. for an additional 2 hr. The reaction mixture was cooled to −40° C., and 32.7 g (0.23 mol) of ethyl trifluoroacetate in 50 mL of anhydrous diethyl ether was added dropwise. The reaction mixture was stirred for 1.5 hr after the addition was complete. The supernatant liquid was decanted from the excess lithium wire and neutralized with 500 mL of 2N aqueous hydrochloric acid. The organic layer was separated, and the aqueous layer was extracted with three 75-mL portions of diethyl ether. The combined ethereal extracts were washed successively with 50 mL of saturated sodium bicarbonate solution, 50 mL of water, and 50 mL of brine and dried over anhydrous magnesium sulfate. After filtration, the filtrate was concentrated on a rotary evaporator and the residue was vacuum distilled to afford 36.4 g (82%) of 4 as a colorless liquid: bp 78° C. (19 mm); $^1$H NMR (CDCl$_3$) $\delta$ 5.83 (q,J=6.75 Hz,2H), 2.13 (s, 1H), 1.67 (d,J=6.46 Hz, 6H), 1.58 (s, 6H); $^{13}$C NMR (CDCl$_3$) $\delta$ 131.40, 124.17, 125.42 (q,J$_{CF}$=287.60 Hz), 81.59 (q,J$_{CCF}$=26.83 Hz), 13.62, 12.43; IR (neat) 3608, 3486, 2929, 2867, 1279, 1163 cm$^{-1}$; Anal. calcd. for C$_{10}$H$_{15}$F$_3$O C, 57.68; H, 7.26. Found: C, 57.53; H, 7.31.

EXAMPLE 2

Preparation of 1,2,3,4-Tetramethyl-5-(trifluoromethyl)cyclopentadiene (1)(mixture of double-bond isomers)

To 9.65 g (45.3 mmol) of 4 in 250 mL of dry methylene chloride was added 25 mL (385 mmol) of methanesulfonic acid, and the reaction mixture was stirred for 20 s at room temperature, followed by quenching into 300 mL of water. The organic phase was separated, and the aqueous layer was extracted three times with 50-mL portions of methylene chloride. The combined organic layers were washed twice with 50-mL portions of saturated sodium bicarbonate solution, 50 mL of water, and 50 mL of brine and dried over anhydrous magnesium sulfate. After filtration, the filtrate was concentrated on a rotary evaporator and the residue was vacuum distilled to afford 7.2 g (82%) of 1 as a pale yellow liquid: bp 42°–45° C. (4.5 mm); $^1$H NMR (CDCl$_3$) δ 3.26 (q,J=10.05 Hz), 2.99 (q,J=6.71 Hz), 2.66 (q,J=6.85 Hz), 2.07(s), 2.06(s), 2.02(s), 1.92(s), 1.86(s), 1.82(s), 1.79(s), 1.16 (d,J=7.55 Hz), 1.09 (d,J=7.70 Hz); $^{13}$C NMR (CDCl$_3$) δ 149.51 (q,J$_{CCF}$=4.76 Hz), 147.03 (q,J$_{CCCF}$=4.83 Hz), 144.76, 140.53, 140.32, 133.75, 129.26 (q,J$_{CCF}$=30.75 Hz), 128.75, 128.12, 126.54 (q,J$_{CF}$=280.16 Hz), 124.82 (q,J$_{CF}$=269.35 Hz), 123.98 (q,J$_{CF}$=271.17 Hz), 59.30, (q,J$_{CCF}$=26.66 Hz), 53.44, 48.76, 13.73, 13.15, 12.47, 12.08, 11.58, 11.22, 11.13, 11.02, 10.40; IR (neat) 2974, 2938, 2864, 1579, 1358, 1257, 1166, 1098 cm$^{-1}$; MS m/e calcd. for C$_{10}$H$_{13}$F$_3$: 190.0969. Found: 190.0969. Anal. calcd. for C$_{10}$H$_{13}$F$_3$: C, 63.15; H, 6.89. Found: C, 63.30; H, 7.01.

EXAMPLE 3

Preparation of [C$_5$(CF$_3$)(CH$_3$)$_4$]$_2$Os (5)

A mixture of sodium hexachloroosmate (IV) hexahydrate (0.30 g, 0.54 mmol) and 1 (0.66 g, 3.5 mmol) in 25 mL of ethanol was refluxed under an argon atmosphere for 24 hr. After cooling to room temperature, the solvent was evaporated under vacuum and the residue was extracted with hexanes (50 mL) and filtered through a column of neutral alumina (5 cm×2 cm). The eluent solvent was evaporated under vacuum to give a white powder which was dissolved in warm ethanol (ca. 2 mL) and cooled to −78° C. for 3 days. The white precipitate was filtered and washed with pentane (2×1 mL) and dried under vacuum to give 0.80 g of 5 in 26% yield: mp (sealed tube) 241° C.; $^1$H NMR (CDCl$_3$) δ 1.75 (s, 12H, 3,4-CH$_3$), 1.87 (br s, 12H, 2,5-CH$_3$); $^{13}$C NMR (CDCl$_3$) δ 10.0 (2,5-CH$_3$), 10.3 (3,4-CH$_3$), 74.2 (q,J$_{CF}$=36.6 Hz, CF$_3$-C), 78.2 (CH$_3$-C), 83.0 (CH$_3$-C), 127.7 (q,J$_{CF}$=269.5 Hz, CF$_3$); $^{19}$F NMR (CDCl$_3$) δ −55.87 (s, CF$_3$); IR (KBr) 2969, 2914, 1428, 1383, 1245, 1154, 1098, 1018 cm$^{-1}$; MS m/e calcd. for C$_{20}$H$_{24}$F$_6$Os: 570.1396. Found, 570.1386. Anal. calcd. for C$_{20}$H$_{24}$F$_6$Os: 42.25; H, 4.25. Found: C, 42.24; H, 4.38.

EXAMPLE 4

Preparation of [C$_5$(CF$_3$)(CH$_3$)$_4$]$_2$Ru (6)

A 250-mL, three-necked flask equipped with a reflux condenser, gas inlet and magnetic stir bar was charged with 100 mL of absolute ethanol, 0.50 g (1.9 mmol) of ruthenium trichloride hydrate, 1.0 g (5.2 mmol) of 1 and refluxed under an argon atmosphere for one day. The solvent was removed under vacuum and the residue was triturated with 250 mL of hexane and filtered through a 10-cm column of basic alumina. The eluent was removed under vacuum to give 0.06 g of 6 as an air stable pale yellow compound in 65% yield. Recrystallization from hot methanol gave an analytically pure sample of 6: mp (sealed tube) 285°–286° C.; $^1$H NMR (CDCl$_3$) δ 1.71 (s, 12H, 3,4-CH$_3$), 1.84 (s, 12H, 2,5-CH$_3$); $^{13}$C NMR (CDCl$_3$) δ 9.69 (2,5 -CH$_3$), 10.04 (3,4,-CH$_3$), 79.52 (q, J$_{CCF}$=35.5 Hz, CF$_3$-C), 84.05 (CH$_3$-C), 87.79 (CH$_3$-C), 127.42 (q,J$_{CF}$=270.0 Hz, CF$_3$); IR (KBr) 2968, 2915, 1430, 1245, 1154, 1097, 1017 cm$^{-1}$; MS m/e calcd. for C$_{20}$H$_{24}$F$_6$Ru: 480.0826. Found, 480.0830. Anal. calcd. for C$_{20}$H$_{24}$F$_6$Ru: 50.10; H, 5.05. Found: C, 50.24; H, 5.13.

EXAMPLE 5

Preparation of [C$_5$(CF$_3$)(CH$_3$)$_4$]Fe(C$_5$H$_5$) (7)

To a solution of freshly cracked cyclopentadiene (0.17 mL, 2.1 mmol) in Et$_2$O (20 mL) at 0° C. was added 1.0 mL of a 2.5M solution of n-BuLi in hexanes (2.5 mmol) under an argon atmosphere. After stirring for 10 min at 0° C., Cp*Fe(CO)$_2$I(9) (0.18 g, 0.38 mmol) was added and the reaction mixture was stirred for 3 days under an argon atmosphere at room temperature. The reaction solution was filtered through Celite in air and was washed with Et$_2$O (20 mL). The solvent was then removed on a rotary evaporator and the residue was sublimed at room temperature (0.01 mm) with use of a water-cooled probe. The sublimate was dissolved in hexanes (20 mL) and filtered through a column of neutral alumina (5 cm×2 cm). The yellow colored eluent was evaporated to dryness under vacuum and the yellow powder was sublimed (0.01 mm, 25° C.) onto a water-cooled probe yielding 0.023 g of 7 (18%): mp (sealed tube) 61°–62° C., $^1$H NMR (CDCl$_3$) δ 1.92 (s, 6H, 3,4-CH$_3$), 2.01 (q, $^5$J$_{HF}$=1.0 Hz, 6H, 2,5-CH$_3$), 3.90 (s, 5H, Cp); $^{13}$C NMR (CDCl$_3$) δ 11.26 (3,4-CH$_3$), 11.32 (br s, 2,5-CH$_3$), 71.0 (Cp), 79.2 (CH$_3$-C), 83.2 (CH$_3$-C), CF$_3$-C (not observed), CF$_3$ (not observed); $^{19}$F NMR (CDCl$_3$) δ −52.10 (s,CF$_3$); IR (KBr) 2962, 2918, 1431, 1247, 1148, 1107, 1094, 1019, 816, 506 cm$^{-1}$; MS m/e calcd. for C$_{15}$H$_{17}$F$_3$Fe 310.0632, found: 310.0618. Anal. calcd. for C$_{15}$H$_{17}$F$_3$Fe: C, 58.09; H, 5.52. Found: C, 58.03; H, 5.55.

EXAMPLE 6

Preparation of {[C$_5$(CF$_3$)(CH$_3$)$_4$]Fe(CO)$_2$}$_2$) (8)

A 100-mL, three-necked flask equipped with a reflux condenser, gas inlet, and magnetic stir bar was charged with 4.89 g (25.0 mmol) of iron pentacarbonyl, 2.0 g (10.5 mmol) of 1, and 20 mL of anhydrous octane under a dry nitrogen atmosphere. The mixture was refluxed for 2 days under a nitrogen atmosphere, during which time the solution turned deep red and a film or iron metal deposited on the inside of the flask. After cooling to room temperature, the solvent was evaporated under vacuum, and the residue was triturated with methylene chloride (50 mL) and filtered thorough a 2 cm plug of Celite. Removal of the solvent under vacuum and recrystallization of the residue from a mixture of methylene chloride and hexanes gave 0.85 g (34%) of 8 as a dark purple solid. Samples of 8 contain a trace impurity as indicated by a very weak resonance at δ=1.67 ppm in the $^1$H NMR spectrum in CDCl$_3$ solvent: mp (sealed tube) 260°–262° C.; $^1$H NMR (CDCl$_3$) δ 1.58 (s, 12H, 3,4-CH$_3$), 1.83 (q,$^5$J$_{HF}$=2 Hz, 12H, 2,5-CH$_3$); $^{19}$F NMR (CDCl$_3$) δ−52.79 (s, CF$_3$); IR(CH$_2$Cl$_2$) υ (CO) 1952(s), 1776(s); MS m/e calcd. for C$_{24}$H$_{24}$F$_6$Fe$_2$O$_4$: 602.0279, found: 602.0267.

EXAMPLE 7

Preparation of [C$_5$(CF$_3$)(CH$_3$)$_4$]Fe(CO)$_2$I (9)

A solution of 8 (0.66 g, 1.1 mmol) in 50 mL of chloroform was treated dropwise with a solution of iodine (0.30 g, 1.2 mmol) in 100 mL of chloroform. The reaction mixture was then stirred for 3 hr at room temperature. The solvent was removed under vacuum and the brown residue was dissolved in methylene chloride (ca. 40 mL) and filtered through a column of Celite (3 cm×3 cm) on a coarse glass frit. The column was washed with an additional 100 mL of methylene chloride and the filtrate solution was evaporated under vacuum to about 50 mL and diluted with hexanes (120 mL). Cooling overnight at −5° C. gave brown crystals of 9 (0.21 g). A second crop of 9 (0.35 g) was obtained by evaporation of the mother liquor to about 100 mL and cooling to −40° C. The total isolated yield of 9 was 0.56 g (60%). An analytically pure sample of 9 was obtained by sublimation (0.02 mm Hg, 70°-75° C.) and recrystallization from a mixture of methylene chloride (5 mL) and hexanes (30 mL) at −5° C.: mp (sealed tube) 132°-135° C.; $^1$H NMR (CDCl$_3$) δ 1.58 (s, 6H, 3,4-CH$_3$), 1.82 (br s, 6H, 2,5-CH$_3$) δ (CDCl$_3$) δ 10.71 (q,J$_{CF}$=2 Hz, 2,5-CH$_3$), 10.74, (3,4-CH3), 78.4 (q,J$_{CF}$=36.6 Hz, CF$_3$-C), 99.0 (CH$_3$-C) 99.1 (CH$_3$-C), 124.4 (q,J$_{CF}$=271 Hz, CF$_3$) 213.1 (CO); $^{19}$F NMR (CDCl$_3$) δ −52.78 (s, CF$_3$); IR (CH$_2$Cl$_2$) υ (CO) 2039(s), 1995(s) cm$^{-1}$; MS m/e calcd. for C$_{12}$H$_{12}$F$_3$FeIO$_2$: 427.9182, found: 427.9174, Anal. calcd. for C$_{12}$H$_{12}$F$_3$FeIO$_2$: C, 33.68; H 2.83. Found: 33.69; H, 2.88.

EXAMPLE 8

Preparation of {[C$_5$(CF$_3$)(CH$_3$)$_4$]RhCl$_2$}$_2$ (10)

A 250-mL, three-necked flask, equipped with a reflux condenser, gas inlet, and magnetic stir bar, was charged with 0.50 g (1.9 mmol) of rhodium(III) chloride hydrate, 1.0 g (5.2 mmol) of 1, and 100 mL of anhydrous methanol under an argon atmosphere. The reaction mixture was refluxed for two days under argon as an orange-red solid precipitated from the solution. The reaction mixture was cooled to 0° C., and the precipitate was collected by filtration on a medium glass frit in air, and washed with cold pentane to give 0.69 g (65%) of 10 as an orange-red solid. Recrystallization from a mixture of methylene chloride and ethanol gave an analytically pure sample of 10: mp (sealed tube) >300° C. decomposes; $^1$H NMR (CDCl$_3$) δ 1.71 (s, 12H, 3,4-CH$_3$), 1.89 (q,J$_{HF}$=1 Hz, 12H, 2,5-CH$_3$); $^{13}$C NMR (CDCl$_3$) δ 9.46 (3,4-CH$_3$), 10.11 (q,J$_{CF}$=2 Hz, 2,5-CH$_3$), 97.3 (d,J=8 Hz, CH$_3$-C), 101.4 (m, CH$_3$-C), 124.2 (q,J$_{CF}$=273 Hz, CF$_3$), CF$_3$-C (not observed); $^{19}$F NMR (CDCl$_3$) δ −55.42 (s, CF$_3$); IR (KBr) 2927, 1424, 1241, 1180, 1140, 1026 cm$^{-1}$. Anal. calcd. for C$_{20}$H$_{24}$Cl$_4$F$_6$R$_2$: C, 33.09; H, 3.33. Found: C, 32.93; H, 3.41.

EXAMPLE 9

Preparation of [C$_5$(CF$_3$)(CH$_3$)$_4$]Rh(Cl)$_2$(PPh$_3$) (11)

A solution of 10 (0.13 g, 0.18 mmol) and triphenylphosphine (0.10 g, 0.38 mmol) in 20 mL of methylene chloride was stirred for 1 hr at room temperature. Hexanes (20 mL) were then added to the reaction mixture and the solution was evaporated under vacuum until a red precipitate began to form. After cooling in an ice bath for 1 hr, the red powder was isolated by filtration, washed with hexanes (2×2 mL) and dried under vacuum to give 0.22 g of 3 that cocrystallized with ¼ equiv of CH$_2$Cl$_2$ in 92% yield. Brilliant red needles of 3, free from CH$_2$Cl$_2$ solvent, were obtained by dissolution of the red powder in warm toluene (40 mL), layering the solution with hexanes (40 mL) and allowing the hexanes to diffuse into the toluene layer over a period of 1 week at room temperature: mp (sealed tube) 246° C. (decomposes); $^1$H NMR (CDCl$_3$) δ 1.49 (d,J$_{PH}$=3.0 Hz, 6H, 3,4-CH$_3$), 1.53 (dm J$_{PH}$=4.0 Hz, 6H, 2,5-CH$_3$), 7.35 (m, 9H, ortho- and para-phenyl protons), 7.76 (m, 6H, meta-phenyl protons); $^{13}$C NMR (CDCl$_3$), δ 8.66 (3,4-CH$_3$), 9.38 (2,5-CH$_3$), 80.6 (m, CF$_3$-C), 102.1 (t,J=4.9 Hz, CH$_3$-C), 105.8 (t,J=3.1 Hz, CH$_3$-C), 124.4 (q,J$_{CF}$=273 Hz, CF$_3$), 127.9 (s, meta-phenyl carbons) 128.0 (s,para-phenyl carbons), 130.7 (br s, ipso-phenyl carbons), 134.8 (d,J$_{PC}$=9.8 Hz, ortho-phenyl carbons); $^{19}$NMR (CDCl$_3$) δ −54.87 (s, CF$_3$); IR (KBr) 3059, 2919, 1436, 1243, 1180, 1125, 1097, 1022, 697, 512 cm$^{-1}$. Anal. calcd. for C$_{28}$H$_{27}$Cl$_2$F$_3$PRh: C, 53.78; H 4.35. Found: C, 53.86; H, 4.30.

EXAMPLE 10

Preparation of [C$_5$(CF$_3$)(CH$_3$)$_4$]Rh(CO)$_2$ (12)

To a 200-mL Schlenk flask equipped with a magnetic stir bar was added [Cp$^\dagger$RhCl$_2$]$_2$ (10) (1.1 g, 1.5 mmol), Zn dust (0.31 g, 4.74 mmol) and 100 mL of anhydrous methanol. The reaction mixture was heated to reflux with vigorous stirring under an atmosphere of carbon monoxide for 4 hr. After cooling to room temperature, the reaction mixture was filtered and the solvent was removed on a rotary evaporator to given an oily red residue. The red oil was dissolved in pentane and the solution was filtered through a column of alumina (2×10 cm) and an orange-red band was collected. The solvent was removed on a rotary evaporator to give a red oil which was frozen at −78° C. and then placed under vacuum (10$^{-2}$ mm) for 30 min. The orange-red solid was then sublimed onto a water-cooled probe (25° C., 10$^{-2}$ mm) to give 0.55 g (52%) of 12 as a light sensitive, air stable solid. $^1$H NMR (CDCl$_3$) δ 2.08 (s, CH$_3$, 6H), 2.14 (q,J$_{HF}$=1.4 Hz, CH$_3$, 6H); $^{13}$C NMR (CD$_2$Cl$_2$) δ 10.81 (s, CH$_3$), 4.25 (q, J$_{CF}$=2.4 Hz, CH$_3$), CF$_3$-C was not observed, 100.0 (d, J$_{RhC}$=3.7 Hz, CH$_3$-C), 105.7 (d, J$_{RhC}$=4.9 Hz, CH$_3$-C), 125.0 (q, J$_{CF}$=269.8 Hz, CF$_3$), 191.9 (d, J$_{RhC}$=84.2, CO); IR (cyclohexane) υ (CO) 2044, 1982 cm$^{-1}$; MS m/e calcd. for C$_{12}$H$_{12}$F$_3$O$_2$Rh 347.9844, found: 347.9844. Anal. calcd. for C$_{12}$H$_{12}$F$_3$O$_2$Rh; C, 41.40; H, 3.47. Found: C, 41.53; H, 3.52.

EXAMPLE 11

Preparation of [C$_5$(CF$_3$)(CH$_3$)$_4$]Co(CO)$_2$ (13)

To a 50-mL Schlenk flask was added 1 (1.73 g, mmol) Co$_2$(CO)$_8$ (1.8 g, 5.26 mmol), 1,3-cyclohexandiene (0.75 g, 9.4 mmol) and 20-mL of methylene chloride. The reaction mixture was heated to reflux under an argon atmosphere for 7 hr. After cooling to room temperature, the solvent was evaporated under vacuum and the residue was triturated with hexanes (2×20 mL) and chromatographed on a column of neutral alumina (3×30 cm). Two major components were eluted. An initial yellow band was attributed to (η$^3$-cyclohexadienyl)Co(CO)$_3$(IR η(CO) 2056, 1988 cm$^{-1}$), and a red band was attributed to [C$_5$(CF$_3$)(CH$_3$)$_4$]Co(CO)$_2$ (13). Following evaporation of the solvent from the red eluent, 0.45 g of [C$_5$(CF$_3$)(CH$_3$)$_4$]Co(CO)$_2$ was obtained in 14% yield as an air sensitive red oil. $^{19}$F NMR (CDCl$_3$) −49.16; IR (hexanes) ν(CO) 2026, 1969 cm$^{-1}$. MS (low resolution) m/e 304 (M$^+$), 276 (M$^+$—CO), 248 (M$^+$—2CO).

EXAMPLE 12

Preparation of [C$_5$(CF$_3$)(CH$_3$)$_4$]Mo(CO)$_3$I (14)

A 300-mL Schlenk flask equipped with a magnetic stir bar was charged with tolueneumolybdenumtricarbonyl (0.82 g, 3.01 mmol) and 50 mL of anhydrous tetrahydrofuran under a dry argon atmosphere. To this mixture was added 0.61 g (3.20 mmol) 1 via syringe. The reaction mixture was stirred for an additional 8 hr. Trifluoroiodomethane (3.5 g, 17.9 mmol) was then added via syringe and the reaction was stirred for 8 hr. The solvent was removed under vacuum and the residue was triturated with hexane and passed through a plug of Celite. Removal of the solvent under vacuum gave 1.1 g (72%) of 14 as a red solid: mp (sealed tube) 164°–166° C., $^1$H NMR (CDCl$_3$) δ 2.21 (s, 6H), 2.17 (s, 6H); $^{13}$C (CDCl$_3$) δ 237.32, 220.09, 124.38 (q, J$_{CF}$=272.1 Hz), 112.66, 105.81, 96.37 (q,J$_{CCF}$=36.4 Hz), 11.59, 11.48; IR (CH$_2$Cl$_2$) 3054, 2042 (CO), 1971 (CO), 1264 cm$^{-1}$. Anal. calcd. for C$_{13}$H$_{12}$F$_3$IMoO$_3$: C, 31.48; H, 2.44. Found: C, 31.48; H, 2.72.

EXAMPLE 13

Preparation of Cis-3-Methyl-1,1,1-trifluropent-3-en-2-one (15)

A 500-mL, round-bottomed, three-neck flask equipped with a reflux condenser, gas inlet, addition funnel, and magnetic stir bar was charged with 2.75 g (396 mmol) of lithium wire and 200 mL of anhydrous diethyl ether under a dry argon atmosphere. The reaction mixture was cooled to 0° C. and 25.45 g (188 mmol) of freshly prepared cis-2-bromo-2-butene in 50 mL of anhydrous diethyl ether was added dropwise from the addition funnel. After addition was complete, the reaction was allowed to warm to room temperature and stirred for 2 hr. The reaction mixture was transferred to an addition funnel attached to a round-bottomed, three-necked flask fitted with an overhead stirrer, gas inlet, and containing 27.60 g (230 mmol) of lithium trifluoroacetate and 100 mL of anhydrous diethyl ether cooled to −78° C. After addition of the anion was completed, the reaction was stirred at −78° C. for 1 hr. The reaction was quenched by pouring into a separatory funnel containing 400 mL of 2N aqueous hydrochloric acid solution. The organic layer was separated and the aqueous layer was extracted with three 75-mL portions of diethyl ether. The combined ethereal extracts were washed with three 50-mL portions of saturated sodium bicarbonate solution, 50 mL of water, 50 mL of brine, and dried over anhydrous magnesium sulfate. The solution was filtered and the ether was removed by distillation through a ten-inch Vigreaux column at atmospheric pressure. Distillation of the residue under reduced pressure yielded 20.05 g (72%) of (CDCl$_3$) δ 7.04 (q,J=6.95 Hz, 1H), 1.97 (d,J=6.98 Hz, 3H), 1.87 (s, 3H); $^{13}$C NMR (CDCl$_3$) δ 181.40 (q,J$_{CCF}$=33.19 Hz), 145.86 (q, J$_{CCCF}$=3.3 Hz), 132.52, 116.69 (q, J$_{CF}$=1146 cm$^{-1}$; MS m/e calcd. for C$_6$H$_7$F$_3$O 152.0499, found, 152.0449. Anal. calcd. for C$_6$H$_7$F$_3$O: C, 47.38; H, 4.64, found: C, 47.40; H, 4.66.

EXAMPLE 14

Preparation of 3,5-Dimethyl-4-(trifluoromethyl)-1,1,1-trifluorohepta-2-cis-5-dien-4-ol (16)

A 500-mL, round-bottomed, three-necked flask equipped with a gas inlet and magnetic stir bar was charged with 250 mL of anhydrous diethyl ether and 13.09 g (55.47 mmol) of 3-iodo-1,1,1-trifluoro-2-butene under a dry argon atmosphere. The reaction mixture was cooled to −78° C. and 30 mL of 1.4N methyllithium-diethyl ether solution was added via cannula from a graduated Schlenk flask. After addition was complete, the reaction was stirred for 3 min. and 6.09 g (40 mmol) of 15 was added. The reaction was stirred for 1 hr at −78° C. and quenched by pouring into a separatory funnel containing 100 mL of 2N aqueous hydrochloride acid solution. The organic layer was separated and the aqueous layer was extracted twice with 75-mL portions of diethyl ether. The combined ethereal extracts were washed with 50 mL of saturated sodium bicarbonate solution, 50 mL of water, 50 mL of brine and dried over anhydrous magnesium sulfate. The solution was filtered and the solvent was removed on a rotary evaporator. Vacuum distillation of the residue afforded 8.5 g (81%) of 16 as a clear, colorless liquid; bp 69°–72° C. (6 mm). An analytical sample was prepared by preparative GLC at 120° C.: $^1$H NMR (CDCl$_3$) δ 6.11 (q,J=8.34 Hz, 1H), 5.90 (m, 1H), 2.33 (s, 1H), 1.86 (s, 3H), 1.70 (d,J=6.72 Hz, 3H), 1.60 (s, 3H); $^{13}$C NMR (CDCl$_3$) δ 145.40 (q,J$_{CCCF}$=5.85 Hz), 130.02, 126.09, 124.56 (q,J$_{CF}$=287.23 Hz), 123.37 (q,J$_{CF}$=271.23 Hz), 119.52 (q,J$_{CCF}$=34.29 Hz), 81.13 (q,J$_{CCF}$=27.69 Hz), 13.90, 1378, 1206; IR (neat) 3612, 3498, 2933, 2871, 1675, 1351, 1278, 1170, 1102 cm$^{-1}$; MS m/e calcd. for C$_{10}$H$_{12}$F$_6$O 262.0792, found, 262.0775. Anal. calcd. for C$_{10}$H$_{12}$F$_6$O: C, 45.81; H, 4.61. Found: C, 45.34; H, 4.67.

EXAMPLE 15

Preparation of 1,2,4-Trimethyl-3,5-bis-(trifluoromethyl)cyclopentadiene (1A) (Mixture of Olefinic Isomers)

A 300-mL, round-bottomed, three-necked flask equipped with a gas inlet and magnetic stir bar was charged with 200 mL methanesulfonic acid and 3 g (11.43 mmol) of 16. The reaction was stirred for 1 hr and quenched by pouring into a separatory funnel containing 300 mL of icewater. The organic layer was separated and the aqueous layer was extracted three times with 30-mL portions of diethyl ether. The combined ethereal extracts were washed twice with 75-mL portions of saturated sodium bicarbonate solution, 50 mL of water, 50 mL of brine and dried over anhydrous magnesium sulfate. The solution was filtered and the solvent was removed by rotary evaporator. Vacuum distillation of the residue afforded 1.39 g (50%) of 1A as a pale yellow liquid: 41°–42° C. (7 mm). An analytical sample was prepared by preparative GLC at 80°0 C.: $^1$H NMR (CDCl$_3$) δ 3.44 (m), 3.16 (m), 2.16 (s), 2.12 (s), 2.05 (s), 2.04 (s), 1.92 (s), 1.89 (s), 1.30 (d,J=7.33 Hz), 1.25 (d,J=7.55 Hz): $^{13}$C NMR (CDCl$_3$) δ 145.22, 140.07, 136.14, 131.38, 125.33 (q,J$_{CF}$=280.92), 123.54 (q,J$_{CF}$=270.27 Hz), 122.93 (q,J$_{CF}$=271.54 Hz), 60.82 (q,J$_{CCF}$=26.92 Hz), 50.7, 46.21, 13.46, 13.33, 13.13, 12.82, 12.42, 12.12, 11.71, 11.38, 11.36; IR (neat) 2988, 2875, 1660, 1375, 1310, 1256, 1232, 1157, 1120, 1008 cm$^{-1}$; MS m/e calc. for C$_{10}$H$_{10}$F$_6$ 244.0687, found:

244.0677. Anal. calcd. for $C_{10}H_{10}F_6$: C, 49.19; H, 4.13. Found: C, 49.52; H, 4.29.

All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A compound of the formula:

and the two endocyclic double bond isomers thereof, wherein $R^1$ is $(C_1-C_5)$perfluoroalkyl, $R^2$ is $(C_1-C_5)$perfluoroalkyl or $(C_1-C_5)$alkyl, $R^3$ is $(C_1-C_5)$perfluoroalkyl or $(C_1-C_5)$alkyl, $R^4$ is $(C_1-C_5)$alkyl and $R^5$ is $(C_1-C_5)$-alkyl, with the proviso that no more than two of $R^1$, $R^2$ and $R^3$ can be $(C_1-C_5)$perfluoroalkyl.

2. The compound of claim 1 wherein $R^1$ is $(C_1-C_5)$perfluoroalkyl and $R^2$, $R^3$, $R^4$ and $R^5$ are $(C_1-C_5)$alkyl.

3. The compound of claim 2 wherein $R^1$ is trifluoromethyl or pentafluoroethyl and $R^2$, $R^3$, $R^4$ and $R^5$ are each methyl or ethyl.

4. The compound of claim 1 wherein $R^1$ and $R^3$ are each $(C_1-C_5)$perfluoroalkyl and $R^2$, $R^4$ and $R^5$ are each $(C_1-C_5)$alkyl.

5. The compound of claim 4 wherein $R^1$ and $R^3$ are each trifluoromethyl or pentafluoroethyl and $R^2$, $R^4$ and $R^5$ are each methyl or ethyl.

6. The compound of claim 1 wherein $R^1$ and $R^2$ are each $(C_1-C_5)$perfluoroalkyl and $R^3$, $R^4$ and $R^5$ are each $(C_1-C_5)$alkyl.

7. The compound of claim 6 wherein $R^1$ and $R^2$ are each trifluoromethyl or pentafluoroethyl and $R^3$, $R^4$ and $R^5$ are each methyl or ethyl.

8. 1,2,3,4-Tetramethyl-5-trifluoromethylcyclopentadiene.

9. 1,2,4-Trimethyl-3,5-bis(trifluoromethyl)cyclopentadiene.

10. 1,2-Bis(trifluoromethyl)-3,4,5-trimethylcyclopentadiene.

11. An organometallic complex of the formula:

wherein $R^1$ is $(C_1-C_5)$perfluoroalkyl, $R^2$ is $(C_1-C_5)$perfluoroalkyl or $(C_1-C_5)$alkyl, $R^3$ is $(C_1-C_5)$perfluoroalkyl or $(C_1-C_5)$alkyl, $R^4$ is $(C_1-C_5)$alkyl and $R^5$ is $(C_1-C_5)$alkyl, with the proviso that no more than two of $R^1$, $R^2$ and $R^3$ can be $(C_1-C_5)$perfluoroalkyl; M is a metal selected from Groups IIIB, IVB, VB, VIB, VIIB, VIII, or IB, n is 1–5 and each L is a ligand selected so that M has a 16-, 17- or 18-electron outer shell configuration; and the salts thereof; with the proviso that when M is Fe, n is 3 and two of L are CO, the remaining L is not H; and with the further proviso that when is 2 and one L is CO, the other L is not $\{\eta^5\text{-}(CF_3)(CH_3)_4\text{-cyclopentadiene}\}Fe(CO)_2$.

12. The complex of claim 11 wherein $R^1$ is $(C_1-C_5)$perfluoroalkyl and $R^2$, $R^3$, $R^4$ and $R^5$ are $(C_1-C_5)$alkyl.

13. The complex of claim 12 wherein $R^1$ is trifluoromethyl and $R^2$, $R^3$, $R^4$ and $R^5$ are methyl.

14. The complex of claim 11 wherein $R^1$ and $R^2$ are $(C_1-C_5)$perfluoroalkyl and $R^3$, $R^4$ and $R^5$ are $(C_1-C_5)$alkyl.

15. The complex of claim 14 wherein $R^1$ and $R^2$ are trifluoromethyl and $R^3$, $R^4$ and $R^5$ are methyl.

16. The complex of claim 14 wherein $R^1$ and $R^3$ are $(C_1-C_5)$perfluoroalkyl and $R^2$, $R^4$ and $R^5$ are $(C_1-C_5)$alkyl.

17. The complex of claim 16 wherein $R^1$ and $R^3$ are trifluoromethyl and $R^2$, $R^3$, and $R^4$ are methyl.

18. The complex of claim 11 wherein M is a Group VIII metal.

19. The complex of claim 18 wherein M is Fe, Ru, Os, Co or Rh.

20. The complex of claim 11 wherein M is a metal from Groups IIIB, IVB, VB, VIB, VIIB or IB.

21. The complex of claim 20 wherein M is Mo.

22. The complex of claim 11 wherein n=3 and each L is a two-electron donor ligand.

23. The complex of claim 22 wherein each L is CO, $PPh_3$, $P(OPh)_3$ or halo.

24. The complex of claim 11 wherein M is not Fe, n is 2, one L is CO or halo and the other L is $[\eta^5\text{-}(CF_3)(CH_3)_4\text{-cyclopentadienide}]M(CO)_2$ or $[\eta^5\text{-}(CF_3)(CH_3)_4\text{cyclopentadienide}]M(halo)_2$.

25. The complex of claim 11 wherein n is 1 and L is $[\eta^5\text{-cyclopentadienide}]$, $[\eta^5\text{-pentamethylcyclopentadienide}]$, $[\eta^5\text{-}(CF_3)(CH_3)_4\text{cyclopentadienide}]$, $[\eta^5\text{-trifluoromethylcyclopentadienide}]$, $[\eta^5\text{-methylcyclopentadienide}]$, $\kappa\eta^5\text{-indenide}]$ or $[\eta^5\text{-fluorenide}]$.

26. The complex of claim 11 wherein n is 1 and L is an $\eta^6\text{-}(C_6\text{-}C_{12})$ arene.

27. The complex of claim 26 wherein the arene is benzene, 1,3,5-trimethylbenzene, toluene, chlorobenzene, hexamethylbenzene, anisole or napthalene.

28. The complex of claim 11 wherein each L is a thiol, cyano, halo, alkoxy, a nitrile, an isonitrile, a divalent sulfide, an ether, a phosphine, a phosphite or an amine.

29. The complex of claim 11 wherein m is Rh, one L is H, one L is Cl and the third L is $[\eta^5\text{-}(CF_3)(CH_3)_4\text{cyclopentadienide}]RhHCl$.

* * * * *

UNITED STATES PATENT AND TRADEMARK OFFICE
CERTIFICATE OF CORRECTION

PATENT NO. : 5,245,064

DATED : Sept. 14, 1993

INVENTOR(S) : Gassman et al.

It is certified that error appears in the above-identified patent and that said Letters Patent is hereby corrected as shown below:

Column 1, line 57, delete "8939" and insert therefore --8938--.

Column 2, line 55, after the words "$(C_1-C_5)$", insert --perfluoroalkyl is trifluoromethyl $(CF_3)$ or--.

Column 4, line 23, delete "(CN)" and insert therefore --(CS)--.

Column 4, line 48, after the words "$(R_2)$", insert --wherein each X is P or $A_s$, each R is $(C_1-C_5)$- --.

Column 6, line 38, delete "cis,trans $[C_pF_{pe}(CO)_2]_2$" and insert therefore --cis,trans-$[C_pF_e(CO)_2]_2$--.

Column 6, line 39, after the letters "Cp", insert --*--.

Column 6, line 53, delete "cyclopentadiene" and insert therefore --cyclopentadienide--.

Column 7, line 14, delete "seem" and insert therefore --seems--.

Column 9, line 23, delete "$(q, J_{ccF}$" and insert therefore --$(q, J_{cccF}$--.

Column 9, line 56, after the letters "OS: ", insert --C,--.

Column 10, line 45, delete " $_2$)" after the number "$_2$)".

Column 10, line 53, delete "or" and insert therefore --of--.

Column 11, line 24, delete "$\beta$" and insert therefore --13$_C$NMR--.

Column 11, line 31, after the word "Found: ", insert --C,--.

Column 11, line 36, delete "flash" and insert therefore --flask--.

Column 14, line 44, delete "flash" and insert therefore --flask--.

UNITED STATES PATENT AND TRADEMARK OFFICE
CERTIFICATE OF CORRECTION

PATENT NO. : 5,245,064

DATED : Sept. 14, 1993

INVENTOR(S) : Gassman et al.

It is certified that error appears in the above-identified patent and that said Letters Patent is hereby corrected as shown below:

Column 11, line 49, delete "$(q, ^{JHF}$" and insert therefore --$(q, ^{5J}HF$--.

Column 11, line 55, delete "$R_2$" and insert therefore --$Rh_2$--.

Column 12, line 16, delete "$19_{NMR}$" and insert therefore --$19_{FNMR}$--.

Column 12, line 31, delete "given" and insert therefore --give--.

Column 12, line 55, delete "cyclohexandiene" and insert therefore --cycloheaxdiene--.

Column 12, line 64, delete "n" and insert therefore --$\mu$--.

Column 13, lines 9 and 10, delete "tolueneumolybdenumtricarbonyl" and insert therefore --toluenemolybdenumtricarbonyl--.

Column 13, line 30, delete "trifluropent" and inser therefore --trifluoropent--.

Column 13, line 32, delete "three-neck" and insert therefore --three-necked--.

Column 13, line 62, after the word "of", insert --15 as a clear, colorless liquid: bp 67°C (180mm). $^1$HNMR--.

Column 13, line 65, after the symbol "=", insert --291.82 $H_z$), 15.54, 11.08; IR (neat) 2937,1705,1637,1199, --.

Column 13, line 66, delete "152.0499" and insert therefore --152.0449--.

Column 14, line 17, delete "hydrochloride" and insert therefore --hydrochloric--.

Column 14, line 59, delete "80°OC" and insert therefore --80°C--.

Column 14, line 65, delete "50.7" and insert therefore --50.76--.

UNITED STATES PATENT AND TRADEMARK OFFICE
CERTIFICATE OF CORRECTION

PATENT NO. : 5,245,064

DATED : Sept. 14, 1993

INVENTOR(S) : Gassman et al.

It is certified that error appears in the above-identified patent and that said Letters Patent is hereby corrected as shown below:

Column 16, line 20, after the word "when", insert --n--.

Column 16, line 56, delete "k" and insert therefore --l--.

Column 16, line 61, delete "napthalene" and insert therefore --naphthalene--.

Column 16, line 65, delete "m" and insert therefore --M--.

Signed and Sealed this

Twenty-eighth Day of May, 1996

Attest:

BRUCE LEHMAN

*Attesting Officer*  *Commissioner of Patents and Trademarks*